United States Patent
Lee et al.

(10) Patent No.: US 11,779,084 B2
(45) Date of Patent: Oct. 10, 2023

(54) METHOD FOR MEASURING FOOT SIZE AND SHAPE BY USING IMAGE PROCESSING

(71) Applicant: PERFITT, INC., Daejeon (KR)

(72) Inventors: Steena Sun Yong Lee, Seoul (KR); Ye Ji Choi, Gyeonggi-do (KR)

(73) Assignee: PERFITT, INC., Daejeon (KR)

( * ) Notice: Subject to any disclaimer, the term of this patent is extended or adjusted under 35 U.S.C. 154(b) by 503 days.

(21) Appl. No.: 16/979,111

(22) PCT Filed: Mar. 11, 2019

(86) PCT No.: PCT/KR2019/002799
§ 371 (c)(1),
(2) Date: Sep. 8, 2020

(87) PCT Pub. No.: WO2019/172728
PCT Pub. Date: Sep. 12, 2019

(65) Prior Publication Data
US 2021/0093050 A1  Apr. 1, 2021

(30) Foreign Application Priority Data
Mar. 9, 2018  (KR) .......................... 10-2018-0028311

(51) Int. Cl.
*A61B 5/107* (2006.01)
*A43D 1/02* (2006.01)
(Continued)

(52) U.S. Cl.
CPC ............ *A43D 1/025* (2013.01); *A61B 5/1074* (2013.01); *G06T 7/0012* (2013.01); *G06T 7/60* (2013.01); *G06T 7/73* (2017.01)

(58) Field of Classification Search
CPC ...... A43D 1/025; A61B 5/1074; A61B 5/743; A61B 5/1079; G06T 7/0012; G06T 7/60;
(Continued)

(56) References Cited

U.S. PATENT DOCUMENTS 6,546,356 B1 *   4/2003   Genest ................... A43D 1/027
                                                      702/153
2004/0168329 A1 *  9/2004   Ishimaru ................. A43D 1/02
                                                       33/3 R
(Continued)

FOREIGN PATENT DOCUMENTS

| KR | 1020050081387 | 8/2005 |
|---|---|---|
| KR | 1020090129271 | 12/2009 |

(Continued)

OTHER PUBLICATIONS

International Search Report; International Application No. PCT/KR2019/002799 dated Jun. 12, 2019.

*Primary Examiner* — Siamak Harandi
(74) *Attorney, Agent, or Firm* — PNKIP LLC

(57) ABSTRACT

A method for measuring foot size and shape by using image processing includes a step of acquiring an image captured by simultaneously photographing a user's foot and an item having a standardized size; and a calculation step of calculating foot size or shape information from the image. The image is captured when at least a part of the user's foot comes in contact with the item.

13 Claims, 21 Drawing Sheets

(51) Int. Cl.
*G06T 7/73* (2017.01)
*G06T 7/00* (2017.01)
*G06T 7/60* (2017.01)

(58) Field of Classification Search
CPC . G06T 7/73; G06T 2207/30196; G06F 18/00; G06V 40/10
See application file for complete search history.

(56) References Cited

U.S. PATENT DOCUMENTS

2006/0201011 A1* 9/2006 Katsu .................... A43D 1/025
33/512
2011/0288446 A1* 11/2011 Hsieh .................. A43B 3/0042
600/592
2018/0160777 A1* 6/2018 Hei .................... G06Q 30/0627

FOREIGN PATENT DOCUMENTS

| KR | 1020150079585 | 7/2015 |
| KR | 1020150082746 | 7/2015 |
| KR | 1020160141688 | 12/2016 |
| WO | 2014037939 | 3/2014 |

* cited by examiner

METHOD FOR MEASURING FOOT SIZE AND SHAPE BY USING IMAGE PROCESSING

CROSS REFERENCE TO RELATED APPLICATIONS

This application is a National Stage of International Application No. PCT/KR2019/002799, having an International Filing Date of 11 Mar. 2019, which designated the United States of America, and which International Application was published under PCT Article 21(2) as WO Publication No. 2019/172728 A1, which claims priority from and the benefit of Korean Patent Application No. 10-2018-0028311, filed on 9 Mar. 2018, the disclosures of which are incorporated herein by reference in their entireties.

BACKGROUND

1. Field

The present disclosure relates to a method for measuring foot size and/or shape by using image processing.

2. Brief Description of Related Developments

In most shoe manufacturing industries, shoes are manufactured by classifying only the size of the foot at 5 mm intervals without classifying the shape of the foot. There is no standardized dimension standard for each company, and even with shoes of the same size, shoes of different brands sometimes do not fit the feet. In the case of wearing shoes that do not fit the feet like this, symptoms of foot deformation such as hallux valgus may occur due to continuous compression of the shoes, and such deformation of the feet may damage the overall health of the body.

Recently, in order to prevent this risk, the technology in which the shape of a user's foot is three-dimensionally (3D) scanned to manufacture shoes considering several requirements such as the size of the user's foot, the arch, the width of feet, the toe length and the height of the instep of the foot so as to produce shoes that fit exactly to the user's foot, has been developed and used.

SUMMARY

Provided is a method for measuring foot size and/or shape by using image processing.

According to an aspect of the present disclosure, a method for measuring foot size and shape by using image processing, includes acquiring an image captured by simultaneously photographing a user's foot and an item having a standardized size and calculating foot size or shape information from the image. The image may be captured when at least a part of the user's foot comes in contact with the item.

The item may have a rectangular shape, and the image may be photographed when all of four vertices of the item are exposed and the user's foot covers a part of edges of the item.

The calculating of the foot size or shape information from the image may include calculating positions of vertices of the item from the image and calculating a region where the foot is located in the image.

The calculating of the positions of the vertices may include calculating one or more feature points corresponding to a corner from the image, calculating a convex polygon that surrounds a contour of the item from the image and then calculating candidate points of the vertices of the item through a simplification algorithm, and comparing the one or more feature points with the candidate points to select the vertices.

The calculating of the region where the foot is located in the image, may include calculating a first region including a region where the foot and the item do not come in contact with each other, inside a figure formed by the vertices and removing the first region from the image and then calculating a contour of the other region.

The calculating of the foot size or shape information from the image may include calculating a difference between relative lengths of toes from the image to determine a shape type of the foot.

The method may further include, before the acquiring of the image, providing a guide interface to photograph the image when a part of the user's foot comes in contact with the item.

The calculating of the foot size or shape information from the image may include calculating a region where the foot is located in the image and measuring an angle of hallux valgus of the foot from the calculated foot region.

According to another aspect of the present disclosure, there is provided an application program combined with hardware and stored in a computer-readable recording medium to implement the method described above.

Other aspects, features, and advantages than those described above will become apparent from the claims and a detailed description of the present disclosure.

In a method for measuring foot size and shape by using image processing according to an aspect of the present disclosure, a user can measure foot size and/or shape automatically/semi-automatically through an image captured by a user through photographing. Thus, the user can not only easily know information about his/her own foot size conveniently, but also can receive information about shoes that do fit his/her own feet. Of course, the scope of the present disclosure is not limited by these effects.

DETAILED DESCRIPTION

Figure 1:
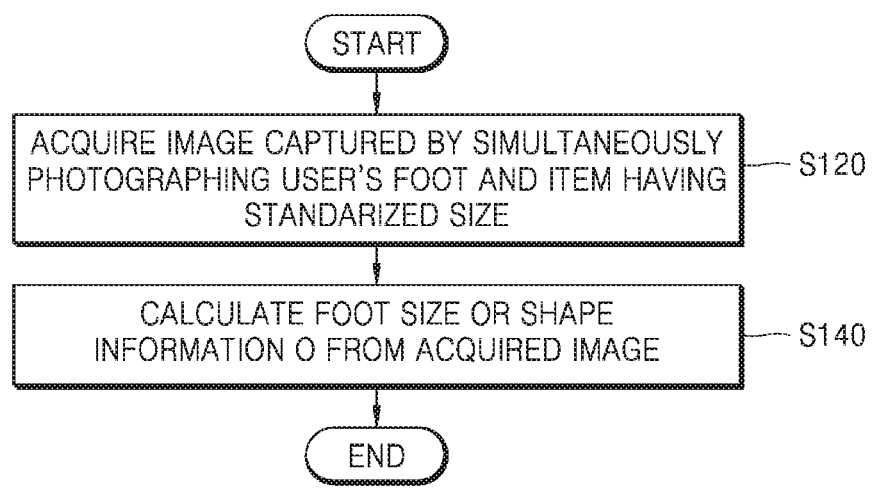
FIG. 1 is a time-sequential flowchart illustrating operations of a method for measuring foot size and shape by using image processing according to an aspect of the present disclosure.

As the present disclosure allows for various changes and numerous aspects, particular aspects will be illustrated in the drawings and described in detail in the written description. The effects and features of the present disclosure, and ways to achieve them will become apparent with reference to aspects to be described later in detail together with the drawings. However, the present disclosure is not limited to the following aspects but may be implemented in various forms.

It will be understood that although the terms "first," "second," etc. may be used herein to describe various components, these components should not be limited by these terms.

As used herein, the singular forms "a," "an," and "the" are intended to include the plural forms as well, unless the context clearly indicates otherwise.

It will be further understood that the terms "comprises" and/or "comprising" used herein specify the presence of stated features or components, but do not preclude the presence or addition of one of more other features or components.

It will be further understood that when a layer, region, or component is referred to as being "formed on," another layer, region, or component, it can be directly or indirectly formed on the other layer, region, or component. That is, for example, intervening layers, regions, or components may be present.

When a certain aspect may be implemented differently, a specific process order may be performed differently from the described order. For example, two consecutively described processes may be performed substantially at the same time or performed in an order opposite to the described order.

Sizes of elements in the drawings may be exaggerated for convenience of explanation. In other words, since sizes and thicknesses of components in the drawings are arbitrarily illustrated for convenience of explanation, the following aspects are not limited thereto.

In the present specification, 'foot size information' or 'shape information' should be interpreted as a concept including all kinds of information about a user's foot. For example, 'foot size information' or 'shape information' refers to quantitative information about the length, the angle, the width, etc. such as the length of the foot, the width of feet, a distance between a specific point on the foot and another point, the width of the foot outline, the angle of three specific points of the foot, and/or qualitative information such as the shape of the outline of the foot, the shape type of the foot, the presence or absence of a foot-related disease, and the degree of the disease, but the 'information' of the present disclosure is not limited thereto.

A method for measuring foot size and shape by using image processing according to an aspect of the present disclosure may be implemented by a measuring apparatus (not shown). The measuring apparatus may correspond to at least one processor or may include at least one processor. Thus, the measuring apparatus may be driven in a form included in other hardware devices such as a microprocessor, a general-purpose computer system, a tablet, or smartphone.

Figure 2:
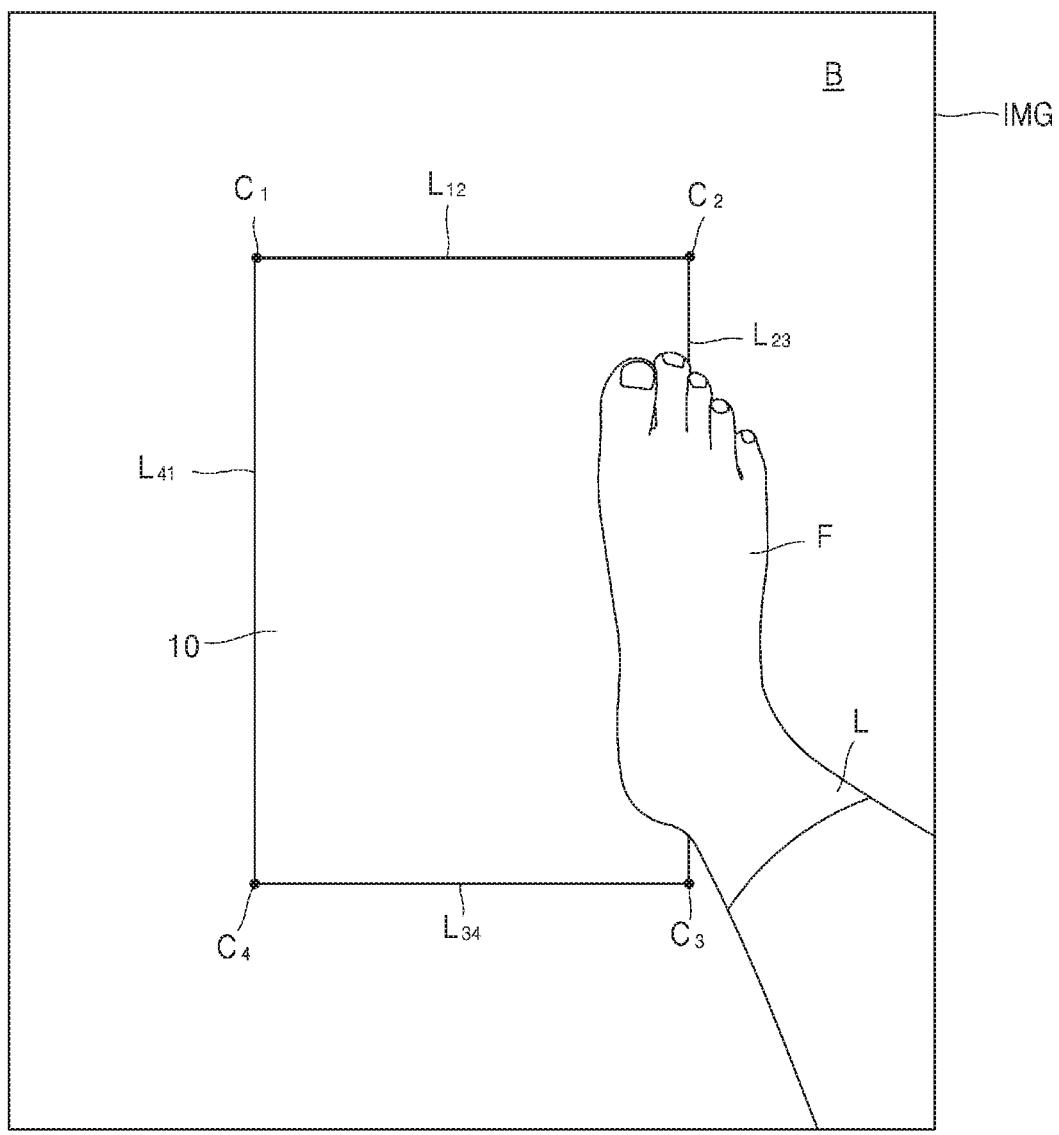
FIGS. 2 and 3 are diagrams schematically showing an image used in the method for measuring foot size and shape by using image processing according to an aspect of the present disclosure.
Figure 3:
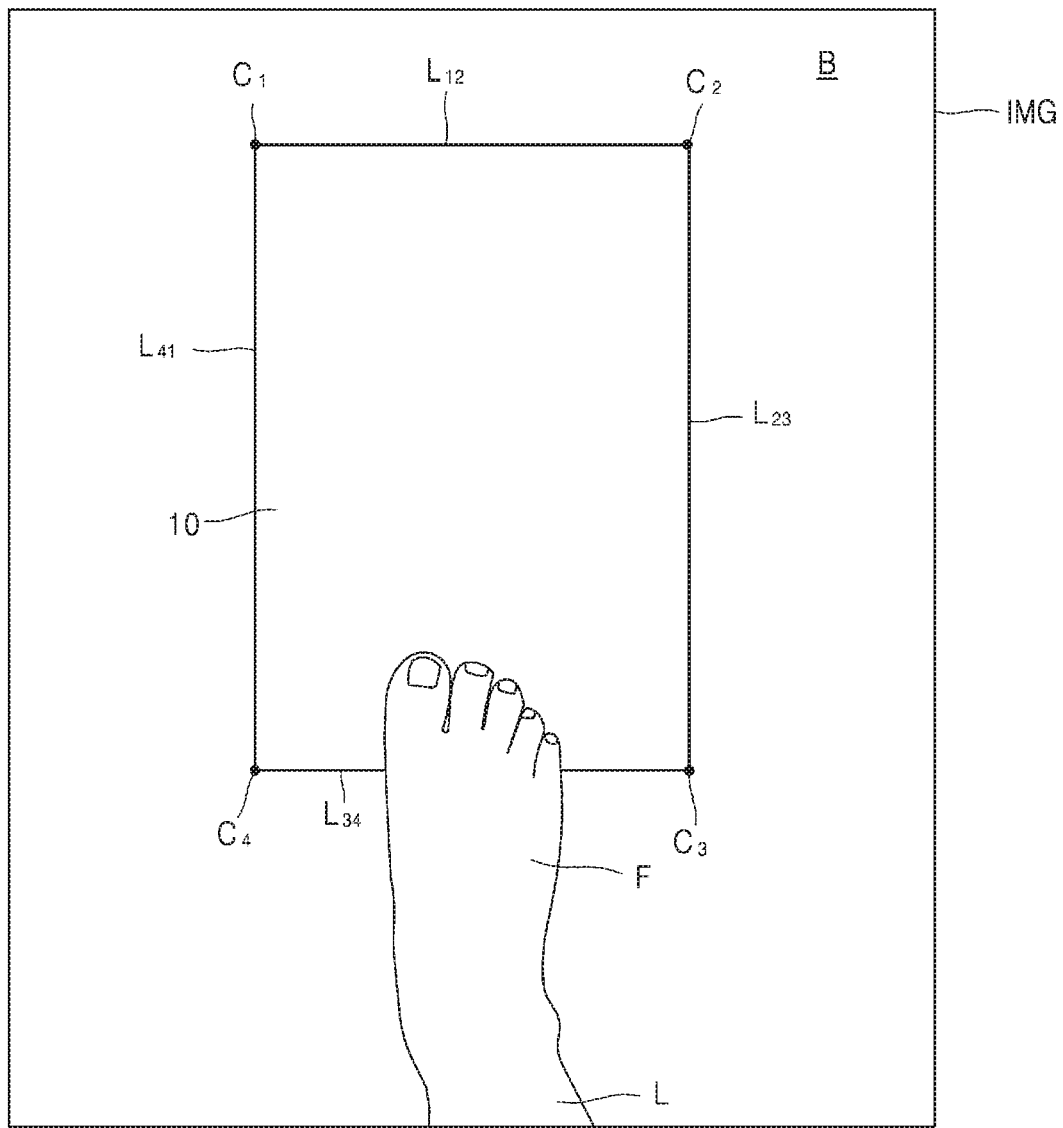

FIG. 1 is a time-sequential flowchart illustrating operations of a method for measuring foot size and shape by using image processing according to an aspect of the present disclosure, and FIGS. 2 and 3 are diagrams schematically showing an image IMG used in the method for measuring foot size and shape by using image processing according to an aspect of the present disclosure. FIGS. 2 and 3 illustrate a state in which there are no other objects than an item 10 and a foot F in a background B of the image IMG for convenience of explanation.

The method for measuring foot size and shape by using image processing according to an aspect of the present disclosure may include acquiring the image IMG captured by simultaneously photographing the user's foot F and the item 10 having a standardized size (S120) and calculating size or shape information of the foot F from the image IMG (S140).

Referring to FIGS. 1 through 3, acquiring of the image IMG captured by simultaneously photographing the user's foot F and the item 10 having the standardized size (S120) may be first performed. The item 10 having the standardized size may be a planar object commonly used in real life such as a paper, an envelope, a notebook, a sketch book, and a file. Hereinafter, it will be described as an example in which the item 10 having the standardized size is an A4 paper having the size of 210 mm×297 mm.

Since, in an aspect of the present disclosure, foot size and shape is measured by using image processing, the image IMG captured by photographing the foot F is essentially used. Although FIGS. 2 and 3 illustrate the image IMG captured by photographing the bare foot F, the image IMG captured by photographing the foot F in socks may also be used. The item 10 having the standardized size may provide a reference for calculating/acquiring size information from the captured image IMG. Thus, the item 10 and the foot F may be simultaneously photographed.

In the present disclosure, the image IMG captured by photographing the user's foot F and the item 10 when at least a part of the user's foot F comes in contact with the item 10, may be image-processed so that the user's foot size may be measured. When the image IMG captured by simultaneously photographing the foot F and the item 10 in the state in which the foot F and the item 10 come in contact with each other, is used, the foot F and the item 10 may be easily distinguished from each other within the image IMG through an image processing algorithm using a color value difference.

In an aspect, the acquired image IMG may be photographed when all of four vertices of the item 10 are exposed and the user's foot F covers a part of edges of the item 10.

Referring to FIG. 2, the image IMG captured in a state in which the user's foot F covers a part of the edges of a vertical length of the A4 paper, is shown. The image IMG used in image analysis may be captured in a state in which both ends of the foot F come in contact with the edges of the A4 paper.

In an aspect of the present disclosure, after coordinates of four vertices $C_1$, $C_2$, $C_3$, and $C_4$ of the item 10 are checked within the image IMG, affine transformation may be performed to be suitable for the original size and shape of the item 10 so that a size reference may be acquired to calculate the size of the foot F within the image IMG. Thus, in the acquired image IMG, all of the four vertices $C_1$, $C_2$, $C_3$, and $C_4$ of the item 10 may be exposed.

In addition, the image IMG may be captured when the foot F covers a part of edges $L_{12}$, $L_{23}$, $L_{34}$, and $L_{41}$ of the item 10. If the image IMG is captured in a state in which the foot F is located in the middle of the item 10, a part of the vertices $C_1$, $C_2$, $C_3$, and $C_4$ of the item 10 may not be seen from the image IMG due to the leg L photographed together with the foot F. In this case, affine transformation, which is a prerequisite for securing the size reference, is not capable of being performed. Thus, the image IMG used in image processing may be captured in a state in which the foot F covers a part of the edges of the item 10 so that all of the four vertices $C_1$, $C_2$, $C_3$, and $C_4$ of the item 10 may be seen.

According to an aspect of the disclosure, the image IMG may be captured in a state in which both ends of the foot F come in contact with vertical edges of the item 10. Referring to FIG. 2, the image IMG captured in a state in which a right vertical edge $L_{23}$ of four edges of the A4 paper comes in contact with the foot F, is shown. Both ends, i.e., the tip of a toe end and the tip of the heel of the foot F may come in contact with the edges. In this case, the four vertices $C_1$, $C_2$, $C_3$, and $C_4$ may be recognized within the image IMG. In the case of using the image IMG shown in FIG. 2, length information of the foot F may be easily calculated through image processing.

According to an aspect of the disclosure, the image IMG may be captured in a state in which both ends of the feet come in contact with horizontal edges of the item 10. Referring to FIG. 3, the image IMG captured in a state in which a lower horizontal edge $L_{34}$ of four edges of the A4 paper comes in contact with the foot F, is shown. Both ends of the feet, i.e., a left end and a right end of the foot F, may come in contact with the edges. In this case, all of the four vertices $C_1$, $C_2$, $C_3$, and $C_4$ may be recognized within the image IMG. When the image IMG shown in FIG. 3 is used, information about the width of the foot F (the length of feet) may be easily calculated through image processing.

The acquired image IMG may be pre-processed. A pre-processing operation may include a black and white image conversion operation, an adaptive sharpening operation, a blurring operation, an adaptive threshold filter application operation, and a pre-processing method is not limited thereto.

Hereinafter, a method of calculating information about the size or shape of the foot from the image IMG through image processing will be described.

Figure 4:
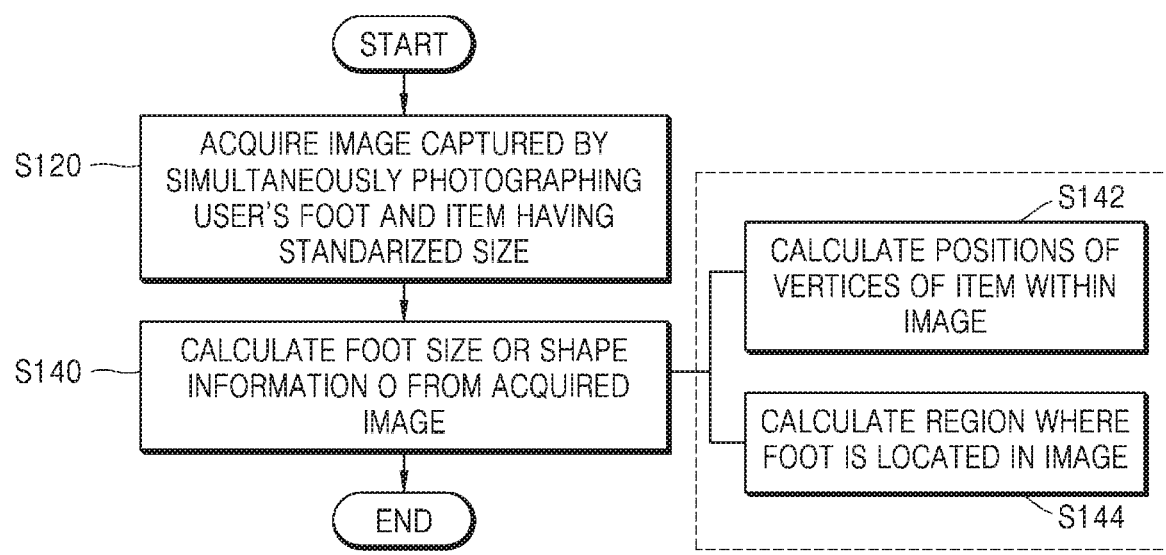
FIG. 4 is a flowchart illustrating a calculating operation according to an aspect of the present disclosure.

FIG. 4 is a flowchart illustrating a calculating operation (S140) according to an aspect. The calculating operation (S140) according to an aspect may include calculating positions of vertices of the item 10 within the image IMG (S142) and calculating a region where the foot F is located in the image IMG (S144).

First, the calculating of the positions of the vertices of the item 10 within the image IMG will be described with reference to FIGS. 5, 6A, 6B, 6C, and 7.

The calculating of the positions of the vertices of the item 10 (S142) according to an aspect may include calculating feature points, calculating candidate points of vertices, and selecting vertices.

Figure 5:
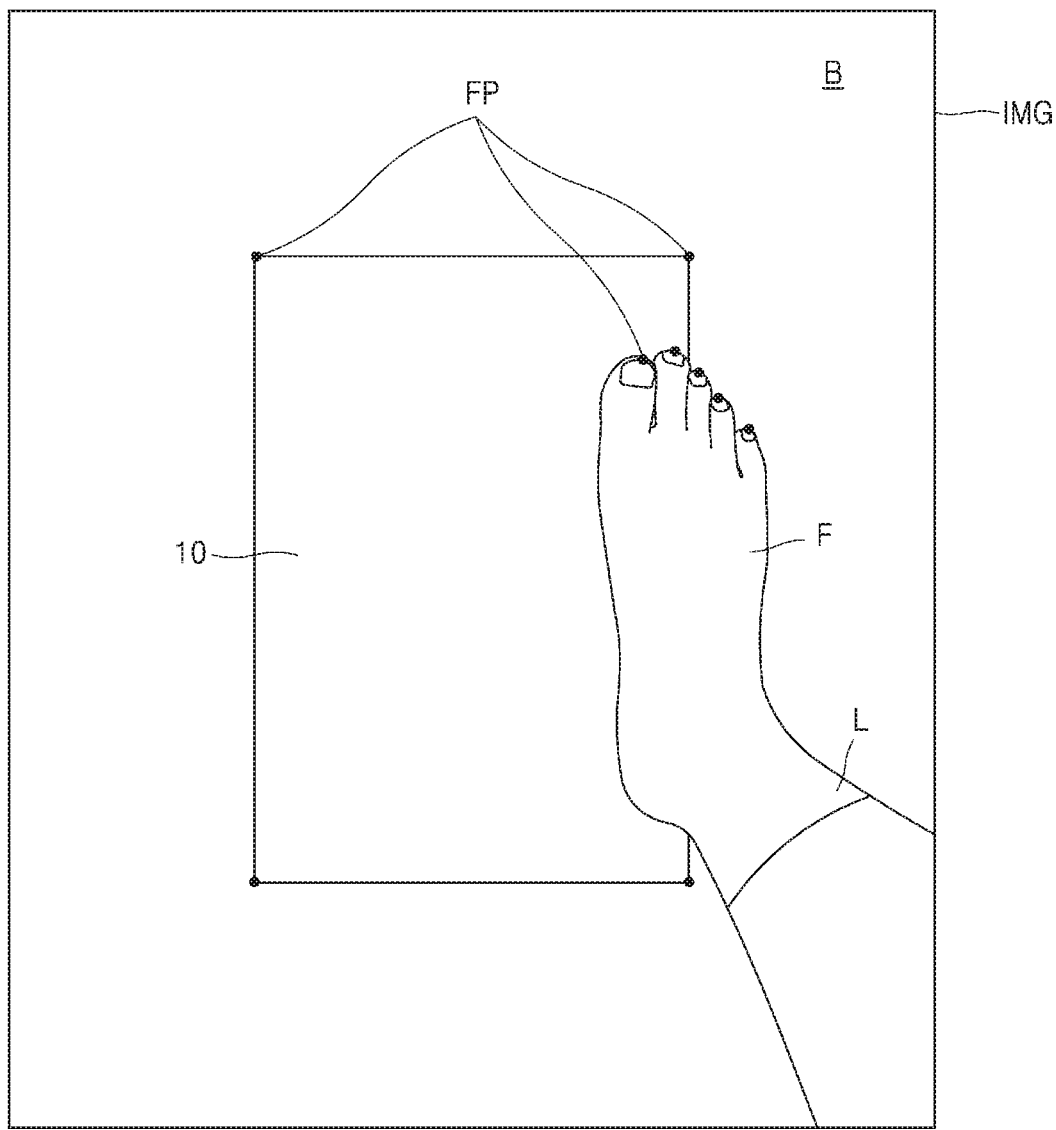
FIG. 5 is a diagram showing an operation of calculating feature points.

FIG. 5 is a diagram illustrating an operation of calculating feature points FP. According to an aspect, the calculating of the positions of the vertices may include calculating one or more feature points FP corresponding to a corner from the image IMG. Referring to FIG. 5, calculating of feature points FP to be determined as a 'corner' from the (pre-processed) image IMG may be performed. In an aspect, a features from accelerated segment test (FAST) algorithm for extracting a corner using brightness information of a plurality of pixels corresponding to a circle boundary around each pixel may be used. An algorithm for calculating feature points FP according to the present disclosure is not limited thereto, and various corner detection algorithms such as Moravec algorithm, Harris algorithm, Shi & Tomasi algorithm, Wang & Brady algorithm, and SUSAN algorithm may be used. In the case of using the corner detection algorithm, feature points FP having the feature of a 'corner' such as an end of a toe in addition to actual vertices of the item 10 may be selected within the image IMG. FIG. 5 illustrates that four vertices of the item 10 and five toe endpoints are calculated as feature points FP.

Figure 6A:
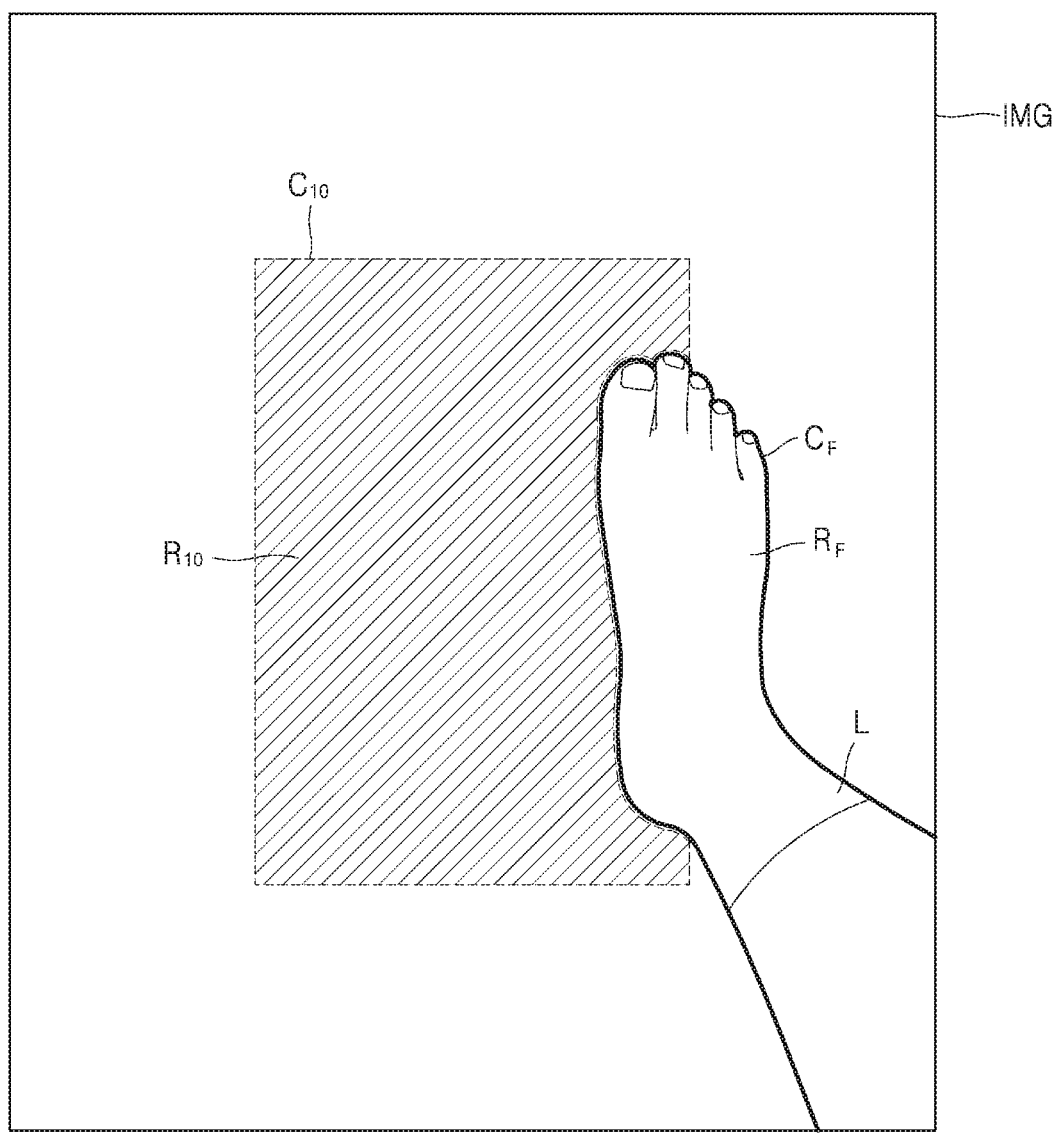
FIGS. 6A through 6C are diagrams sequentially illustrating an operation of calculating candidate points of vertices of an item.
Figure 6B:
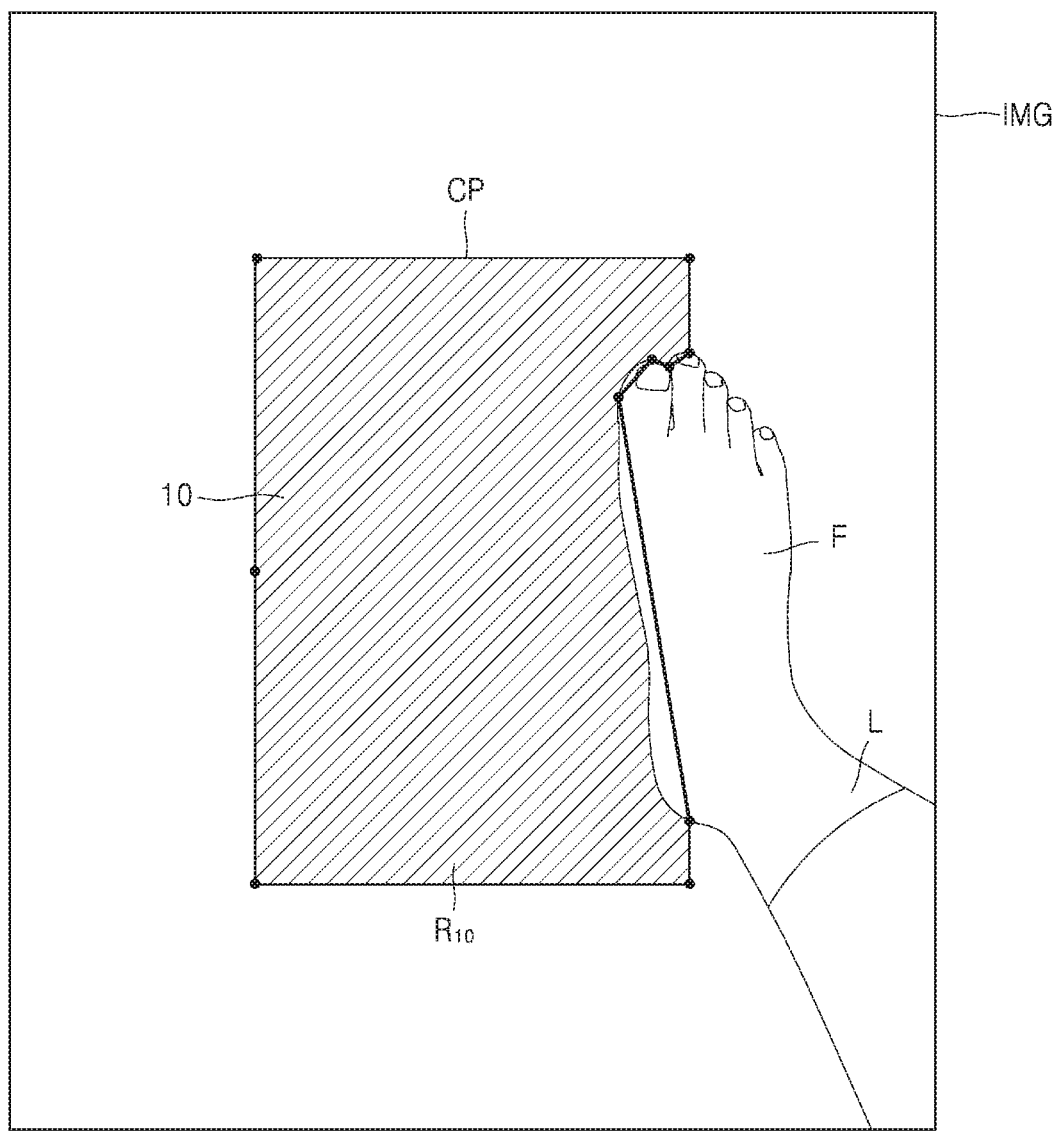
Figure 6C:
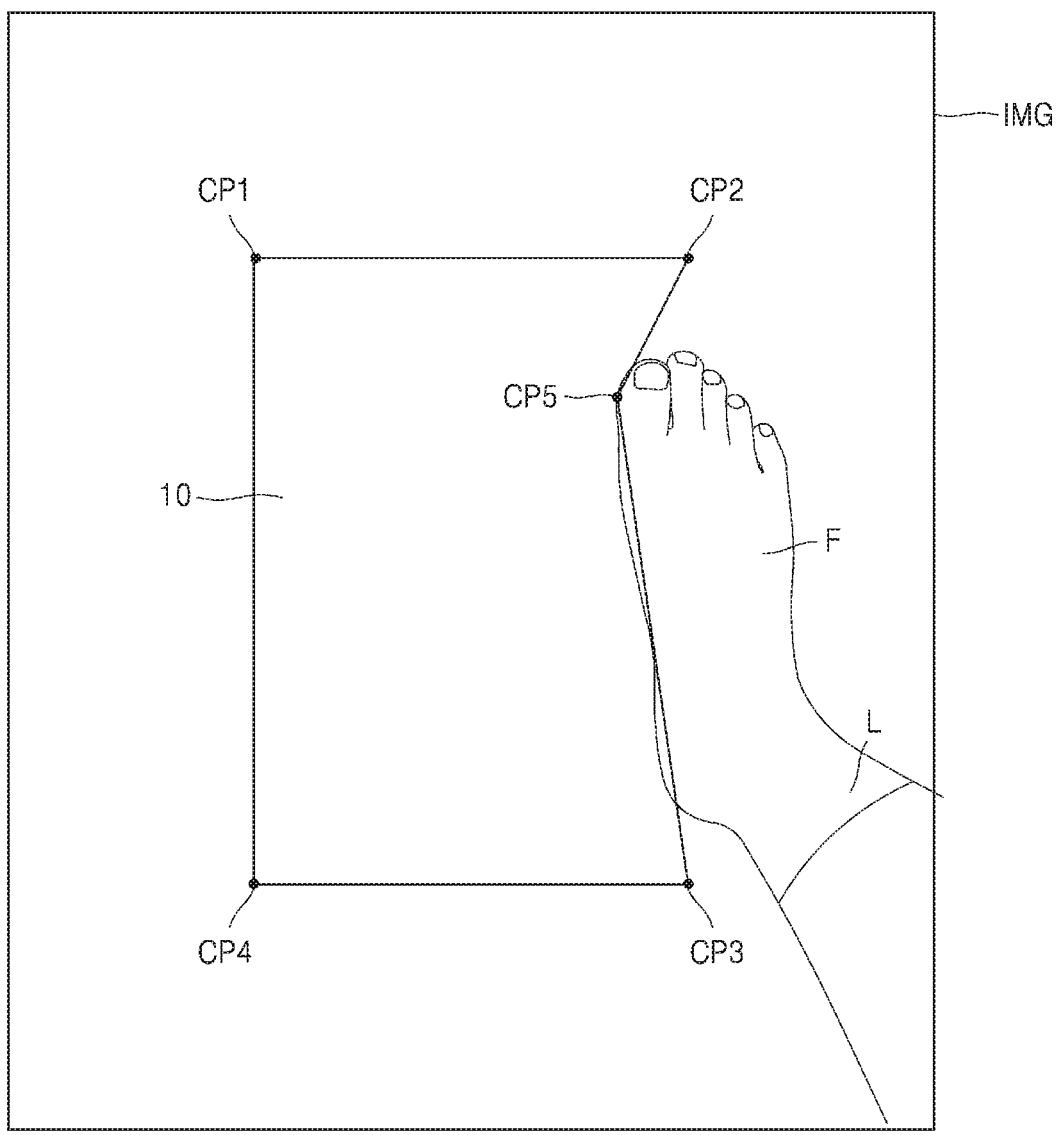

FIGS. 6A through 6C are diagrams sequentially illustrating calculating candidate points of vertices of the item 10.

Referring to FIG. 6A, extracting of a contour from the (pre-processed) image IMG may be performed. In an aspect of the present disclosure, Teh-Chin chain approximation algorithm may be used. However, aspects are not limited thereto. When the extracting of the contour is performed, a contour $C_{10}$ of the item and a contour $C_F$ of the foot may be extracted.

According to an aspect of the present disclosure, after the extracting of the contour is performed, selecting of a closed curve having a largest area among closed curves within the image IMG may be performed. Since, in an aspect of the present disclosure, a A4 paper having a larger size than the foot F is generally used, it may be expected that an inner area $R_{10}$ of the contour $C_{10}$ of the item is larger than an inner area $R_F$ of the contour $C_F$ of the foot. A measuring apparatus may determine the closed curve having a largest area as a closed curve of the 'item 10'.

According to an aspect of the present disclosure, determining whether the ratio of the inner area $R_{10}$ of the closed curve of the item with respect to the entire area of the image IMG is within a preset value, may be performed. In this case, due to the characteristics of the image IMG captured centering on the item 10 and the foot F, it may be expected that the inner area $R_{10}$ of the item 10 in the image IMG is in a specific ratio of the entire area of the image IMG. For example, when the ratio of the inner area $R_{10}$ of the contour with respect to the entire area of the image IMG exceeds about 20% to about 80%, the measuring apparatus may determine that no item 10 is photographed in the image IMG or the contour $C_{10}$ of the item is misrecognized. In this case, the measuring apparatus may provide the user with a guide interface for re-photographing the image IMG and then may re-acquire the image IMG.

Subsequently, referring to FIG. 6B, calculating of a convex polygon P that surrounds the contour of the item 10 may be performed. The convex polygon CP may be a set of points that surround the inner area $R_{10}$ of the item 10 with a smallest area among points forming the contour. Sklansky algorithm may be used to find such a convex polygon CP. However, aspects are not limited thereto. FIG. 6B illustrates that the convex polygon CP including seven points surrounds the inner area $R_{10}$ of the item 10.

Subsequently, referring to FIG. 6C, calculating of candidate points CP of vertices of the item 10 through a simplification algorithm may be performed. As an algorithm for simplifying and expressing a given curve by using fewer points, Douglas-Peucker algorithm, Visvalingam algorithm, etc. may be used. However, aspects are not limited thereto. A plurality of 'candidate points' may be calculated through the simplification algorithm. If the number of 'candidate points' is less than or equal to 3, the measuring apparatus may determine that detection of the item 10 has failed, may provide the user with an interface for guiding to re-photograph the image IMG and then may re-acquire the image IMG. FIG. 6C illustrates that five candidate points CP1 to CP5 have been detected.

Figure 7:
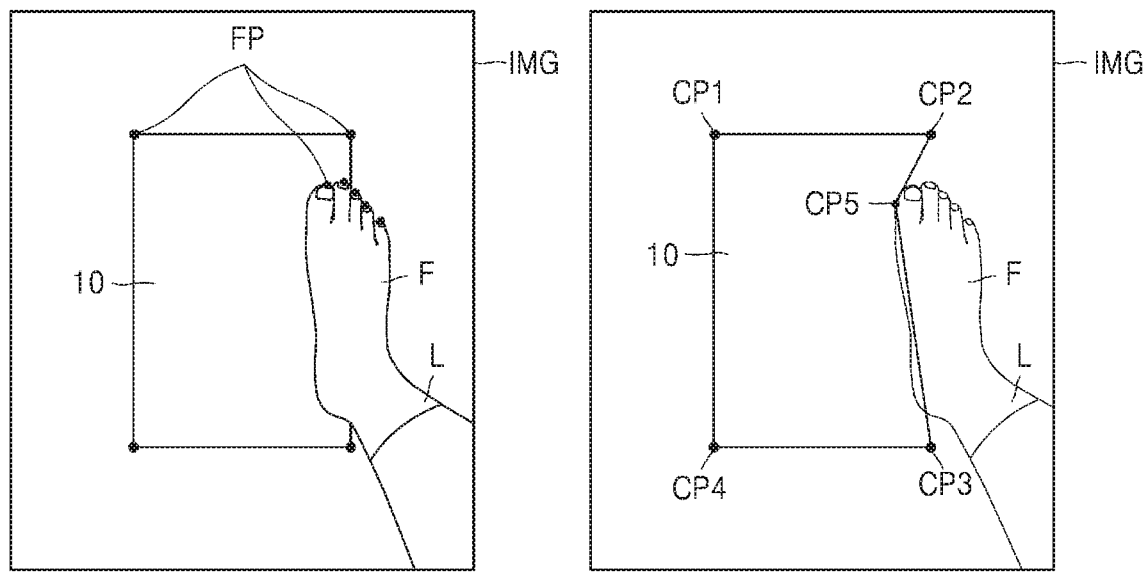
FIG. 7 is a diagram illustrating an operation of selecting vertices of an item.
Figure 7:
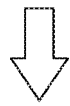
Figure 7:
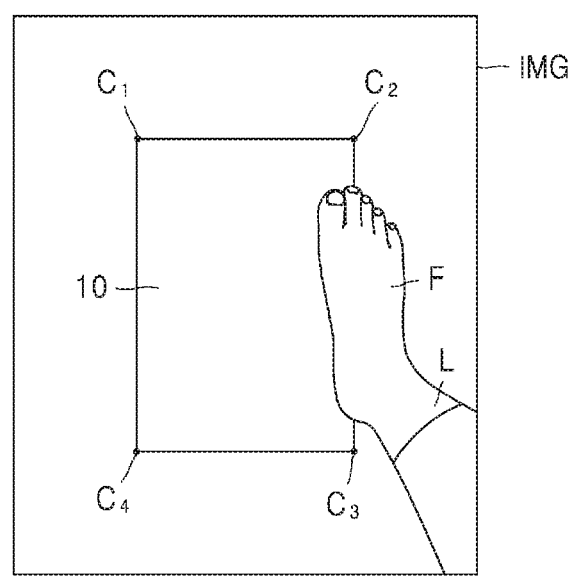

FIG. 7 is a diagram illustrating selecting of vertices $C_1$, $C_2$, $C_3$, and $C_4$ of the item 10. Previously, the 'feature points FP' representing the 'corner' and the 'candidate points CP' for simplifying and representing the shape of the item 10 covered by the foot F have been calculated, respectively, so that positions where the feature points FP and the candidate points CP appear in common, may be finally selected as the vertices $C_1$, $C_2$, $C_3$, and $C_4$. For example, when there are four or more feature points FP and candidate points, only points at corresponding positions are determined and selected as the vertices $C_1$, $C_2$, $C_3$, and $C_4$ through distance comparison between a plurality of feature points FP and a plurality of candidate points.

In addition, as above, a method of automatically selecting four vertices $C_1$, $C_2$, $C_3$, and $C_4$ of the item 10 through image processing has been described. However, an operation of calculating vertices may also be performed with the user's help. For example, the user may select a position near the four vertices of the item 10 by directly touching a display unit (not shown) included in the measuring apparatus or connected to the measuring apparatus. At this time, the measuring apparatus may calculate exact coordinates of the four vertices $C_1$, $C_2$, $C_3$, and $C_4$ by using a FAST algorithm for extracting a corner only near a pixel that the user touches.

After selecting of the four vertices $C_1$, $C_2$, $C_3$, and $C_4$ of the item 10 is performed, affine transformation of the image IMG according to the size of the item 10 may be performed. For example, when the item 10 is an A4 paper, the image IMG may be affine-transformed so that a square formed by the four vertices $C_1$, $C_2$, $C_3$, and $C_4$ selected from the image IMG may correspond to a rectangle having the size of 210 mm×297 mm. Thus, a size reference for acquiring size information of the foot F may be obtained.

Figure 8A:
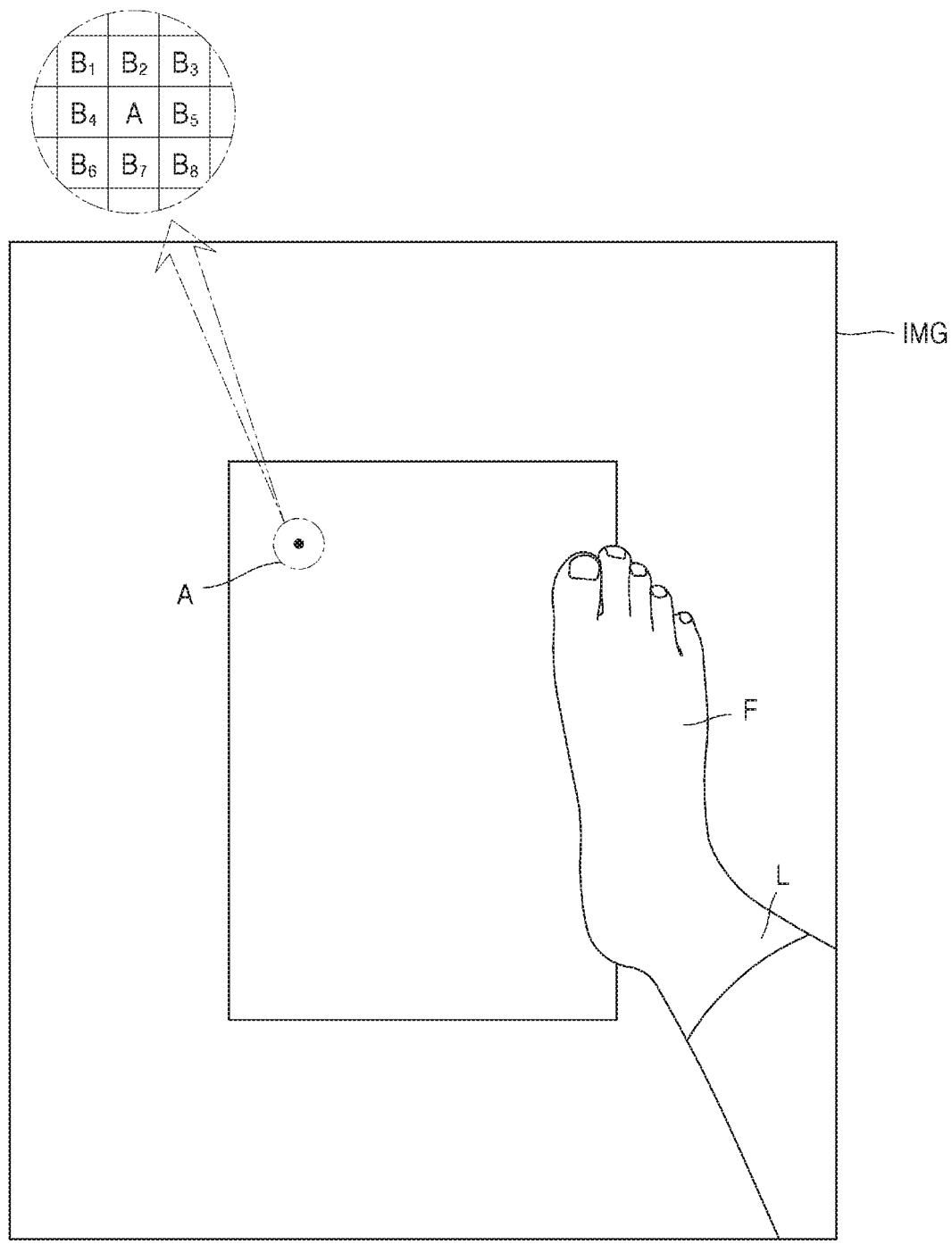
FIGS. 8A through 8C are diagrams sequentially illustrating an operation of calculating a region where the foot is located in an image, according to an aspect of the present disclosure.
Figure 8B:
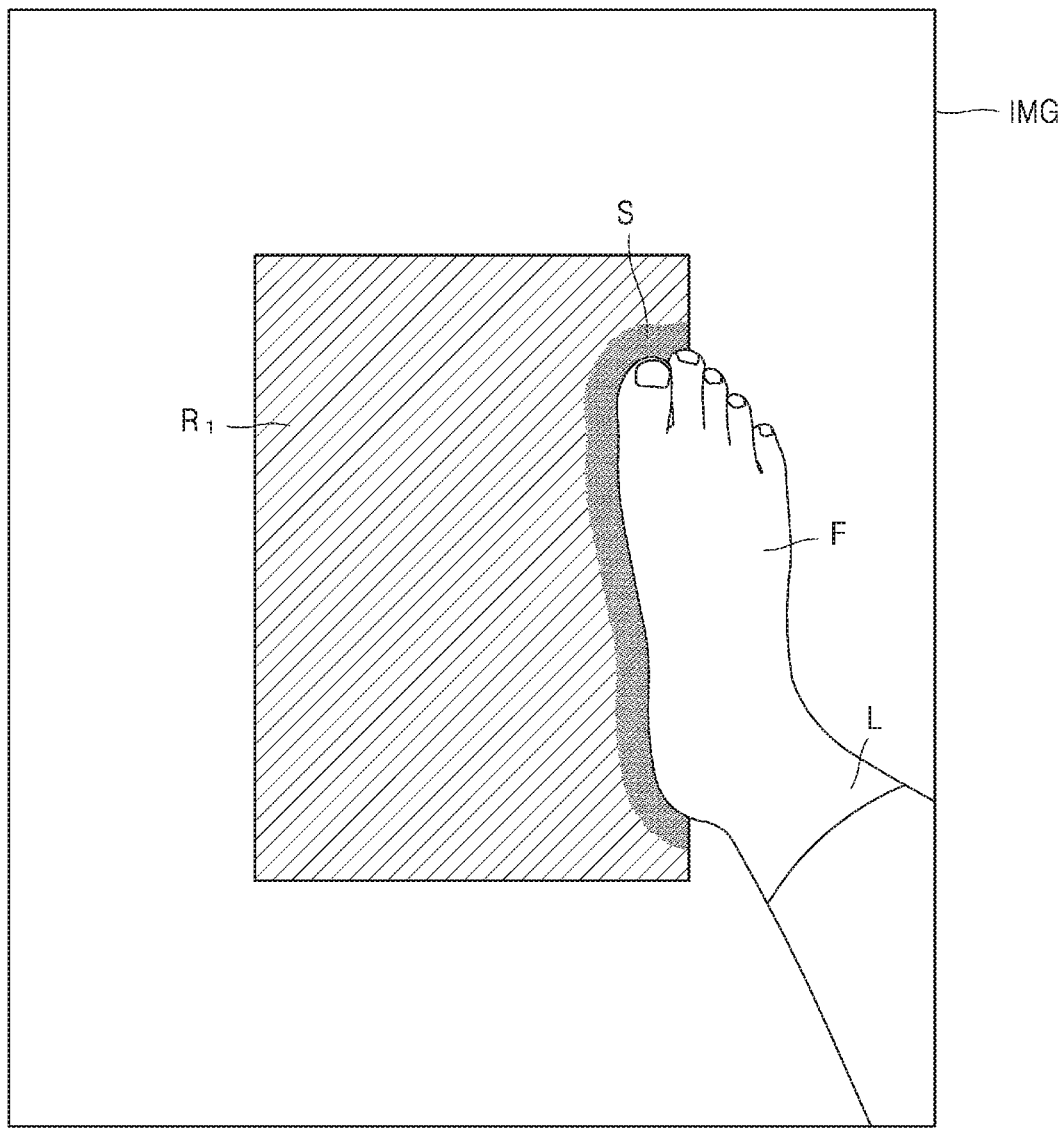
Figure 8C:
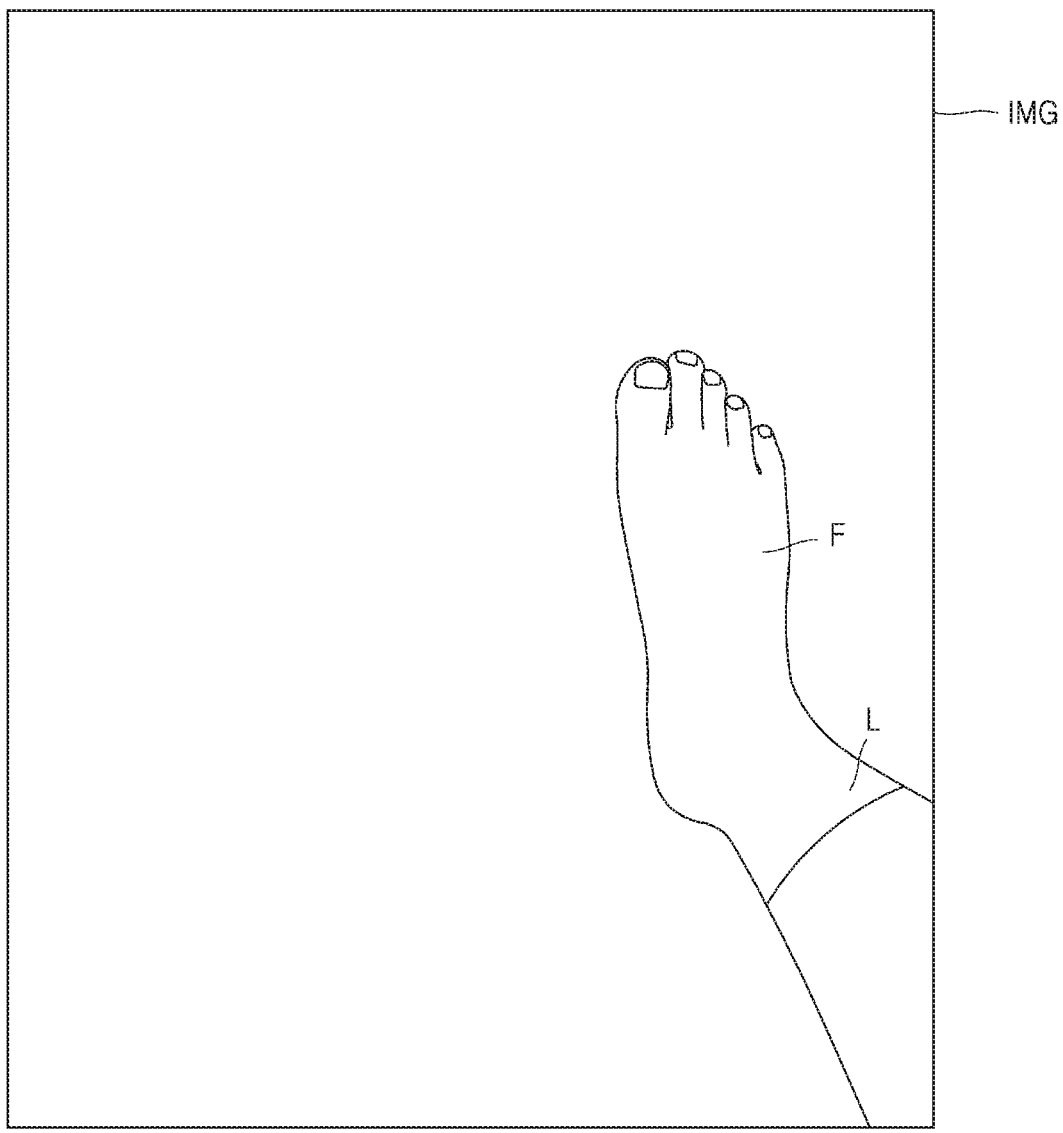

FIGS. 8A through 8C are diagrams sequentially illustrating an embodiment of calculating a region where the foot F is located in the image IMG.

Referring to FIG. 8A, one point or pixel A inside a boundary of the item 10 may be selected. The pixel A may be selected by the user or may be automatically selected as a point having a color value (CV) close to an intrinsic color of the item 10. For example, when the item 10 is an A4 paper, the pixel A may be selected as a pixel having a CV close to white among the central region of the image IMG.

Subsequently, comparing a brightness value of the selected pixel A with brightness values of pixels $B_1$ to $B_8$ around the selected pixel A may be performed. Referring to FIG. 8A, the measuring apparatus may compare a difference between grayscale values of a A-pixel and a $B_1$-pixel, for example. In this case, when a difference between brightness of two pixels is less than or equal to a preset threshold, the measuring apparatus may determine that the two pixels belong to the 'same region'. That is, when the difference between brightness of the A-pixel and $B_1$-pixel is less than or equal to the preset threshold, it may be determined that the A-pixel and the $B_1$-pixel are in the 'same region'. The brightness comparing may be repeatedly performed while the position of a pixel is changed. Finally, as shown in FIG. 8B, a first region $R_1$ that belongs to the 'same region' as the first A-pixel may be calculated. The first region $R_1$ may include a region where the foot F and the item 10 do not come in contact with each other, i.e., a region determined to correspond to the 'item 10'. Since the first region $R_1$ is a region that does not correspond to the 'foot F', the first region $R_1$ may be removed when the region of the foot F is calculated.

In addition, when a shadow S of the foot F is photographed simultaneously in the image IMG captured by photographing the foot F, the shadow S is darkly photographed and thus is not determined to correspond to the 'same region' as the initial 'A-pixel' and may not be included in the first region $R_1$. In this case, according to an aspect of the present disclosure, histogram equalization may be performed in a portion excluding the first region $R_1$ from the image IMG. In this case, a boundary between an actual region of the shadow S and the region of the foot F appear clearly. Thus, the region of the shadow S and the region of the foot F may be clearly distinguished from each other using an edge detection algorithm such as Canny algorithm.

Subsequently, referring to FIG. 8C, after the first region $R_1$ is removed, a contour of the other region may be calculated so that a foot region $R_F$ may be finally calculated and confirmed.

Figure 9A:
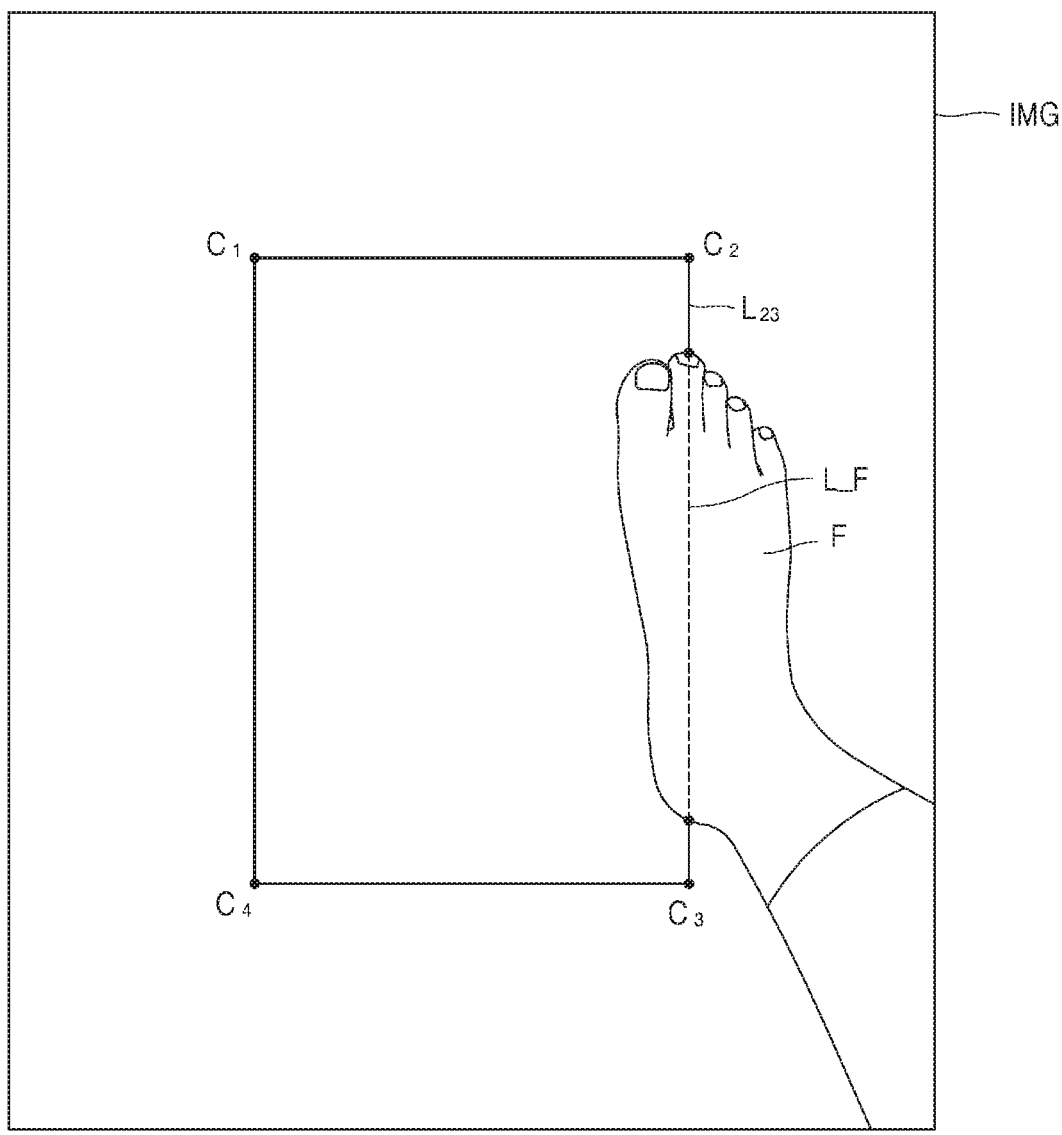
FIGS. 9A and 9B are diagrams illustrating a method for measuring the size of a foot according to an aspect of the present disclosure.
Figure 9B:
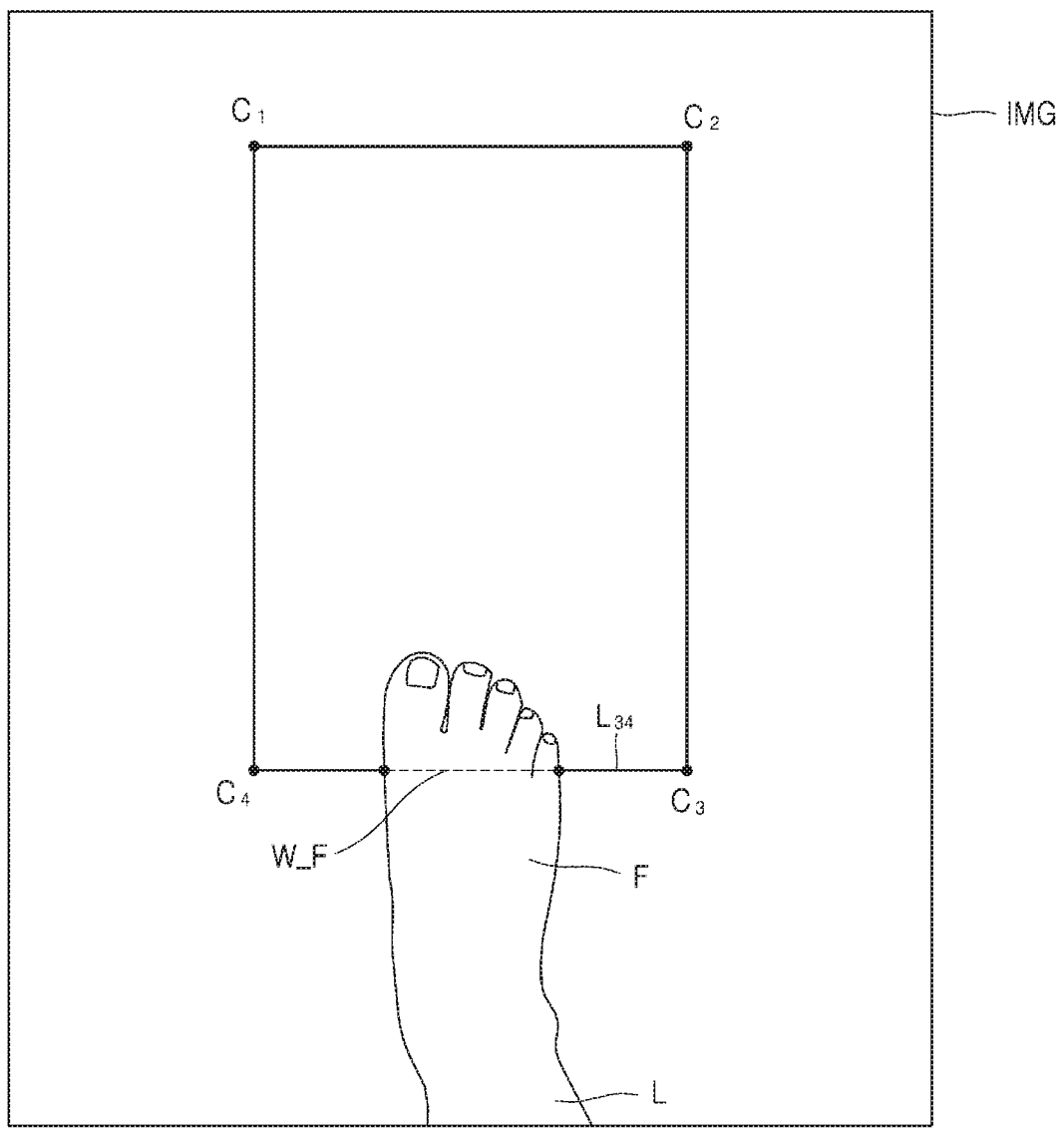

FIGS. 9A and 9B are diagrams illustrating a method for measuring the size of a foot according to an aspect of the present disclosure. After the region of the item 10 and the region of the foot F are calculated through image processing, the foot size such as the length of the foot F and/or the width of feet may be measured using image processing. For example, referring to FIG. 9A, a length of the foot L_F may be measured using the length of a point where the vertical edge $L_{23}$ of the item 10 and the region of the foot F overlap. Referring to FIG. 9B, the width of feet W_F may be measured using the length of a point where the horizontal edge $L_{34}$ of the item 10 and the region of the foot F overlap.

FIGS. 10A-10E are diagrams illustrating various toe shape types. According to an aspect of the present disclosure, calculating may include calculating a difference between relative lengths of toes from the image IMG to determine the shape type of the foot F.

When using pixel differentiation, the endpoint of the toe may be selected. In an aspect of the present disclosure, after the image IMG is divided into regions of interest having a certain pixel, when the presence of the feature points FP within each of the regions of interest is determined and there are feature points FP, increasing the weight of the corresponding pixel and determining the presence of the feature points FP within a larger region of interest may be repeatedly performed so that a point that is likely to be the endpoint of the toe may be calculated.

After five endpoints of the toe are calculated, the shape type of the foot may be determined using a difference between positions of toes. For example, the measuring apparatus may compare the user's toe position data with foot shape type template data that has been previously stored or received from a server, to classify the user's foot type with the least error.

Figure 10A:
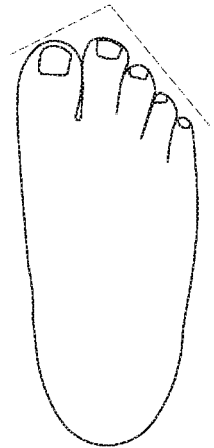
FIGS. 10A-10E are diagrams illustrating various toe shape types.
Figure 10B:
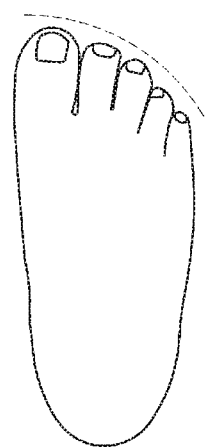
Figure 10C:
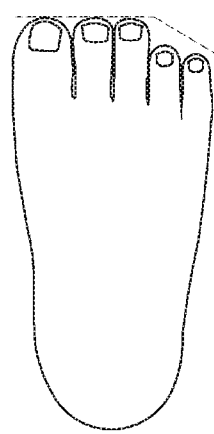
Figure 10D:
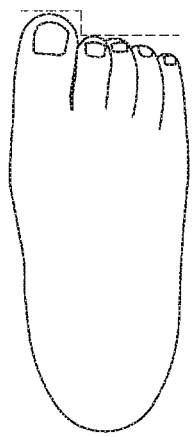
Figure 10E:
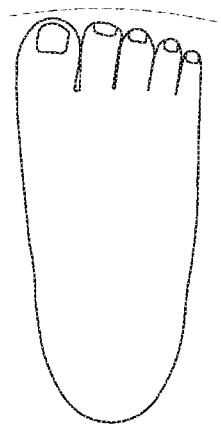

For example, when an index toe is long, as shown in FIG. 10A, the measuring apparatus may classify the user's foot as a first type. When the big toe is long and the length gradually decreases toward the little toe, as shown in FIG. 10B, the measuring apparatus may classify the user's foot as a second type. When the lengths of the big toe, the index toe and the middle toe are similar and the lengths of the ring finger toe and the little toe are short, as shown in FIG. 100, the measuring apparatus may classify the user's foot as a third type. When the length of the big toe is long and the lengths of the other toes are similar, as shown in FIG. 10D, the measuring apparatus may classify the user's foot as a fourth type. When a difference between the lengths of the big toe and the index toe is not large, as shown in FIG. 10E, the measuring apparatus may classify the user's foot as a fifth type. The above-described foot types are exemplary, and a foot shape classification method of the present disclosure is not limited thereto. In addition, the measuring apparatus may determine whether the user has hallux valgus using the shape information of the foot, which will be described later with reference to FIGS. 15 and 16.

Figure 11:
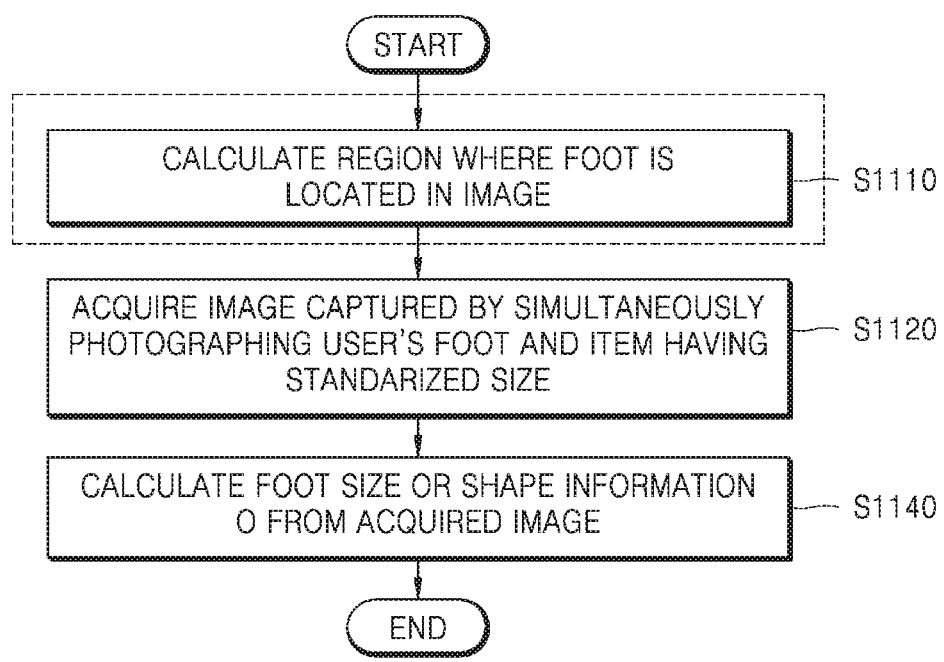
FIG. 11 is a time-sequential flowchart illustrating operations of a method for measuring foot size and shape by using image processing according to an aspect of the present disclosure.
Figure 12:
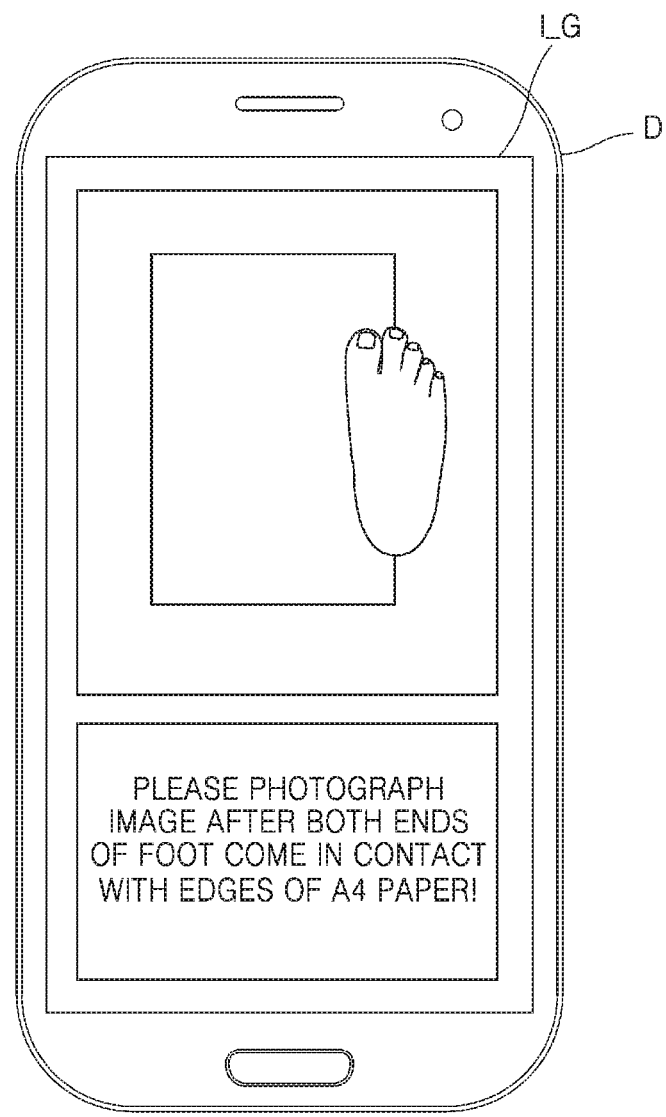
FIG. 12 is a diagram illustrating an interface for guiding a photographing method.

FIG. 11 is a time-sequential flowchart illustrating operations of a method for measuring foot size and shape by using image processing according to an aspect of the present disclosure, and FIG. 12 is a diagram illustrating an interface for guiding a photographing method.

The method for measuring the foot size and shape by using image processing according to an aspect of the present disclosure may further include, before acquiring of the image IMG (S1120), providing a guide interface to photograph the image IMG when a part of the user's foot F comes in contact with the item 10 (S1110).

Referring to FIGS. 11 and 12, the measuring apparatus may provide/display an interface I_G for guiding a method of photographing the image IMG. Referring to FIG. 12, the measuring apparatus may provide the guide interface I_G for photographing an image "when at least a part of the user's foot comes in contact with the item" by using a photo, a text, etc. displayed on a terminal D. In detail, the measuring apparatus may provide the guide interface I_G to photograph the image so that four vertices of the item may not be covered by the user. In more detail, the measuring apparatus may provide the photographing method guide interface I_G to photograph the image by placing the foot on the edges of the A4 paper.

Subsequently, when the user photographs the image IMG according to the photographing method guided by the interface, the measuring apparatus may acquire the image IMG (S1120) and may calculate the foot size or shape information through image processing (S1140). If the user does not have an item or photographs an image 'incorrectly' so that the four vertices of the item 10 are not visible, the measuring apparatus that fails to detect the four vertices may provide a guide interface to re-photograph the image.

Figure 13:
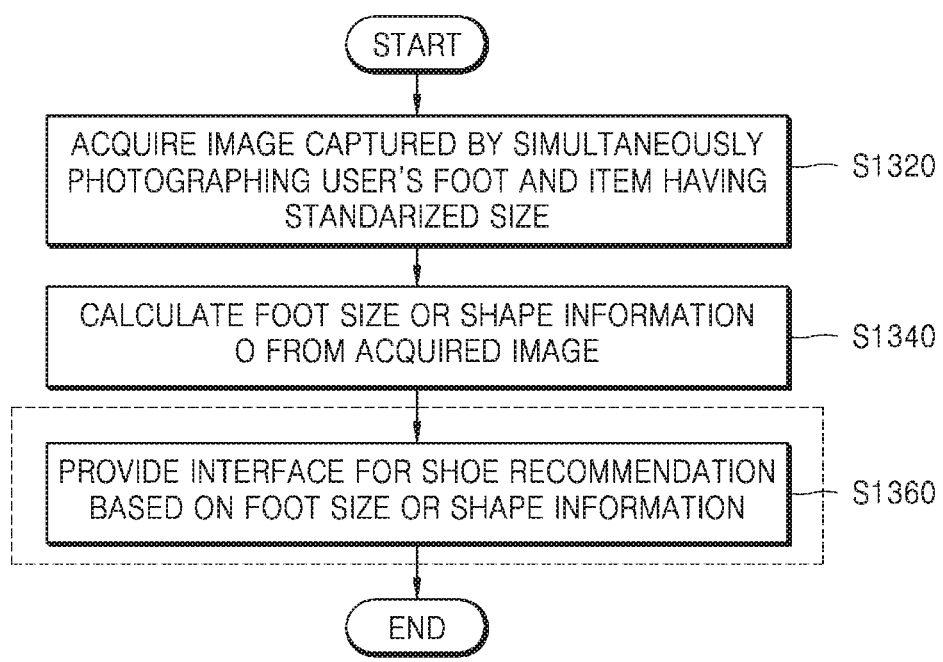
FIG. 13 is a time-sequential flowchart illustrating operations of a method for measuring foot size and shape by using image processing according to an aspect of the present disclosure.
Figure 14:
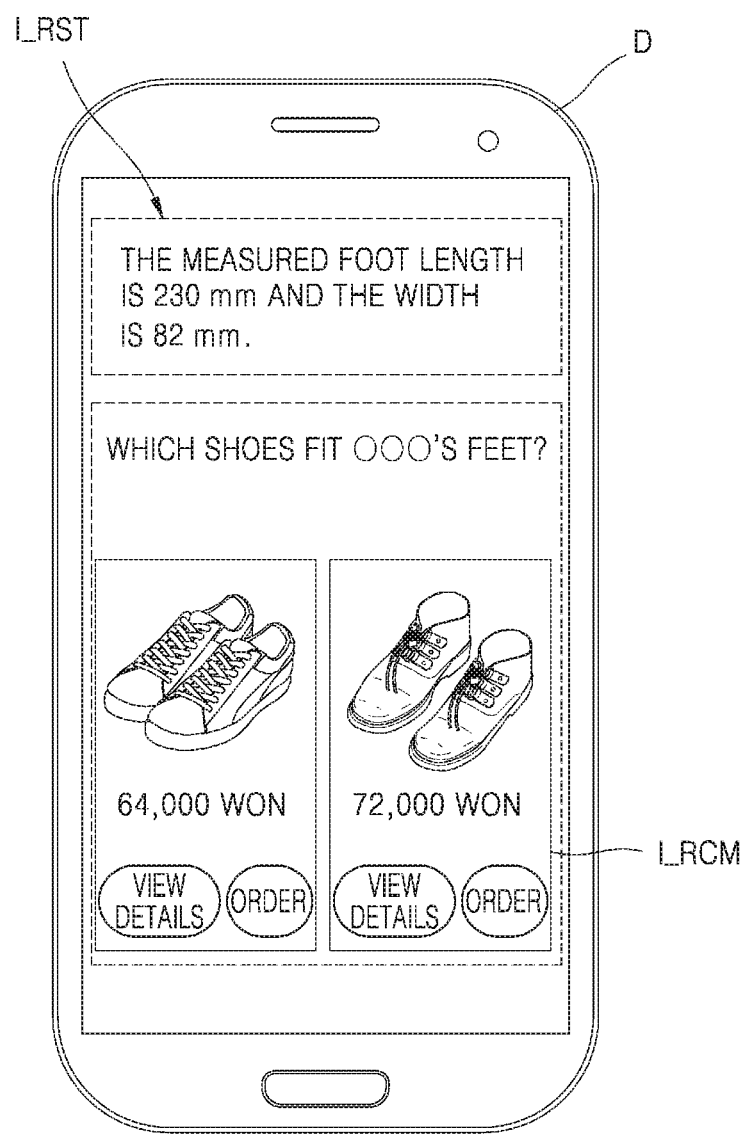
FIG. 14 is a diagram illustrating an interface for providing information about foot and shoes.

FIG. 13 is a time-sequential flowchart illustrating operations of a method for measuring foot size and shape by using image processing according to an aspect of the present disclosure, and FIG. 14 is a diagram illustrating an interface for providing information about foot and shoes.

The method for measuring the foot size and shape by using image processing according to an aspect of the present disclosure may further include, after acquiring of an image IMG (S1320) and calculating of the size or shape information of the foot F (S1340) are performed, providing an interface I_RCM for shoe recommendation based on the size or shape information of the foot F (S1360).

Referring to FIG. 14, the measuring apparatus may provide an image processing result interface I_RST. In addition, the measuring apparatus may provide a shoe recommendation interface I_RCM for recommending shoes suitable for the user's foot based on the size information such as the user's foot length, the width of feet and/or shape information obtained through image processing. The shoe recommendation interface I_RCM may display information such as the photo and price of the shoes. In this case, shoes exposed to the shoe recommendation interface I_RCM may be shoes having an inner surface suitable for the user's foot size and/or shape. At this time, the measuring apparatus may provide the shoe recommendation interface I_RCM matching the user's foot size information acquired through image processing by receiving the shoe size information of various brands from a previously-stored database or server.

Figure 15:
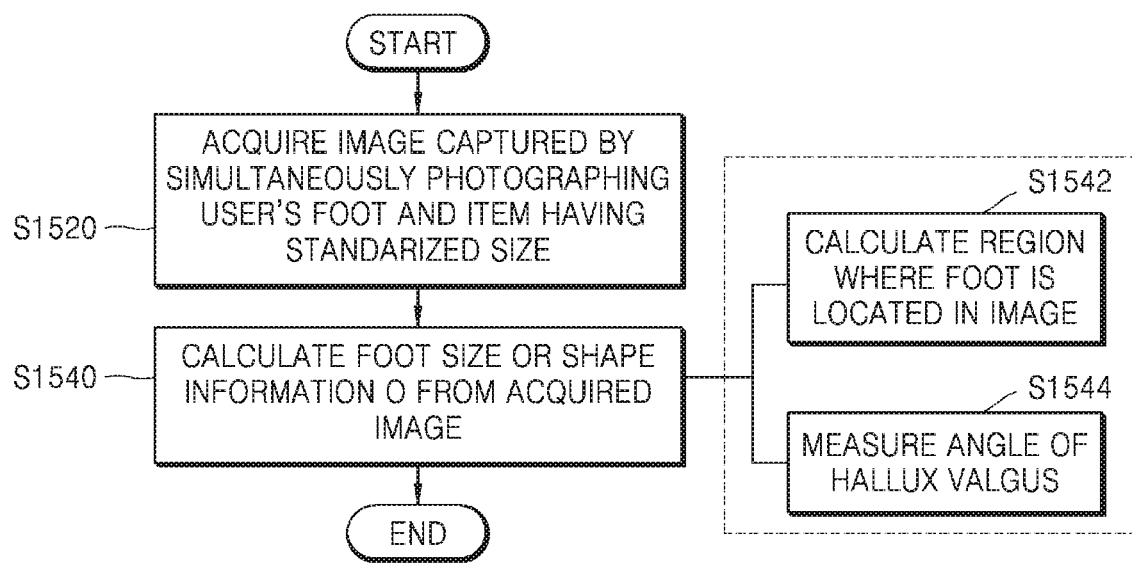
FIG. 15 is a time-sequential flowchart illustrating operations of a method for measuring foot size and shape by using image processing according to an aspect of the present disclosure.
Figure 16:
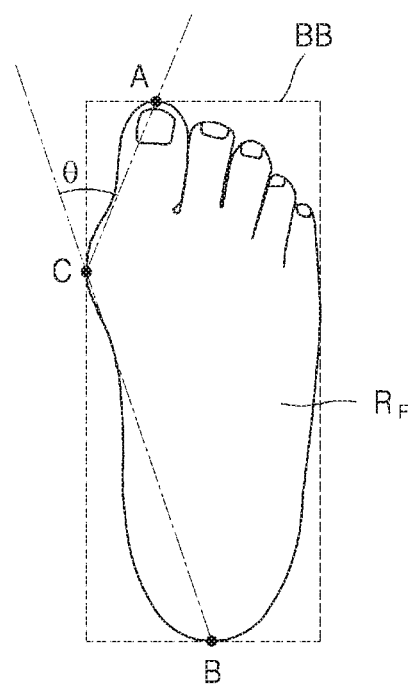
FIG. 16 is a diagram illustrating a method for measuring an angle of hallux valgus.

FIG. 15 is a time-sequential flowchart illustrating operations of a method for measuring foot size and shape by using image processing according to an aspect of the present disclosure, and FIG. 16 is a diagram illustrating a method for measuring an angle of hallux valgus. In an aspect of the present disclosure, the angle of hallux valgus of a patient with the symptom of hallux valgus, which is bent while the big toe joint is protruding, may be measured so that the severity of thereof may be determined.

The method for measuring the foot size and shape by using image processing according to an aspect of the present disclosure may include acquiring an image IMG captured by simultaneously photographing the user's foot F and the item 10 having a standardized size (S1520) and calculating size or shape information of the foot F from the image IMG (S1540). At this time, the calculating (S1540) according to an aspect of the present disclosure may include calculating a region where the foot F is located in the image IMG (S1542) and measuring an angle of hallux valgus of the foot from the calculated foot region (S1544).

Referring to FIGS. 15 and 16, the measuring apparatus may calculate a region $R_F$ where the foot is located, and then may calculate a bounding box BB that surrounds the foot region $R_F$. For example, the bounding box BB may be a rectangle having a minimum width surrounding the foot region $R_F$. In this case, the bounding box BB and the foot region $R_F$ may come in contact with each other at each of a point A where the big toe protrudes upward, an endpoint B of the heel, and a point C where the big toe joint protrudes laterally. In an embodiment of the present disclosure, an angle $\theta$ formed by a line connecting the point A and the point C and a line connecting the point B and the point C may be measured as an angle of hallux valgus. A method for measuring the angle of hallux valgus is not limited thereto.

The measuring apparatus may determine the severity of hallux valgus after measuring the angle $\theta$ of hallux valgus. The measuring apparatus may classify the severity of hallux valgus into 'steps' according to the size of the angle of hallux valgus. For example, the measuring apparatus may determine the severity as '0 step' when the angle $\theta$ of hallux valgus is less than or equal to 12 degrees. The measuring apparatus may determine the severity as '1 step' when the angle $\theta$ of hallux valgus is 12 to 20 degrees. The measuring apparatus may determine the severity as 'step 2' when the angle $\theta$ of hallux valgus is 20 to 30 degrees. The measuring apparatus may determine the severity as 'step 3' when the angle $\theta$ of hallux valgus is 30 to 50 degrees. The measuring apparatus may determine the severity as 'step 4' when the angle $\theta$ of hallux valgus is greater than or equal to 50 degrees. The number and numerical values of the above steps are exemplary and do not limit the present disclosure.

The measuring apparatus may provide an interface indicating severity information of hallux valgus. For example, the measuring apparatus may provide an interface displaying information 'this step is an initial step of a hallux valgus symptom and thus please pay attention to shoe selection', when the measured severity is at step 1. In addition, the measuring apparatus may provide an interface for recommending shoes that are comfortable for hallux valgus patients or a hospital specializing in hallux valgus or displaying lifestyle information required for hallux valgus patients, based on the angle θ of hallux valgus or information about the severity of hallux valgus.

The method according to the above-described aspect may be implemented in the form of programs and application program instructions that can be executed through various computer means, and recorded in a computer-readable medium. The computer-readable medium may include program instructions, data files, data structures, and the like alone or in combination. The program instructions recorded on the medium may be specially designed and configured for the embodiment, or may be known and usable to those skilled in computer software. Examples of computer-readable recording media include magnetic media such as hard disks, floppy disks, and magnetic tapes, optical media such as CD-ROMs and DVDs, magneto-optical media such as floptical disks, and a hardware device specially configured to store and execute program instructions such as ROMs, RAMs, flash memory, and the like. Examples of the program instructions include not only machine language codes such as those produced by a compiler, but also high-level language codes that can be executed by a computer using an interpreter or the like. The above-described hardware device may be configured to operate as one or more software modules to perform the operation of the aspect, and vice versa.

The above-described method of the present disclosure can be executed through an application program stored in a computer-readable recording medium in combination with hardware such as a mobile device such as a smartphone and a tablet. For example, the user photographs the foot F and the item 10 by using a camera built into the smartphone and uploads it to the application program. The application program may analyze the image uploaded/input by the user, measure the size and shape of the user's foot, and recommend shoes matching the user's foot size information.

In the method for measuring foot size and shape by using image processing according to an aspect of the present disclosure, the user can measure the foot size and/or shape automatically/semi-automatically through an image captured by a user through photographing. Thus, the user can not only easily know information about his/her own foot size conveniently, but also can receive information about shoes that do fit his/her own feet.

While the present disclosure has been particularly shown and described with reference to exemplary aspects thereof, it will be understood by those of ordinary skill in the art that various changes in form and details may be made therein without departing from the spirit and scope of the present disclosure as defined by the following claims.

According to the present disclosure, a method for measuring foot size and shape by using image processing is provided. In addition, embodiments of the present disclosure may be applied to an industrially used apparatus for measuring the inner size of an object in which an inner space is formed, by using image processing.

What is claimed is:

1. A method for measuring foot size and shape by using image processing, the method comprising:
acquiring an image captured by simultaneously photographing a user's foot and an item having a standardized size; and
calculating foot size or shape information from the image, wherein the image is captured when at least a part of the user's foot comes in contact with the item,
wherein the calculating of the foot size or shape information from the image comprises:
calculating positions of vertices of the item from the image; and
calculating a region where the foot is located in the image,
wherein the calculating of the region where the foot is located in the image, comprises:
calculating a first region including a region where the foot and the item do not come in contact with each other, inside a figure formed by the vertices; and
removing the first region from the image and then calculating a contour of the other region,
wherein the calculating of the first region comprises:
selecting one point or one pixel inside a boundary of the item;
comparing a brightness value of the selected point or pixel with brightness values of points or pixels around the selected point or pixel;
determining that the selected point or pixel and the points or pixels around the selected point or pixel are in the same region, when a difference between brightness of the selected point or pixel and the points or pixels around the selected point or pixel is less than or equal to the preset threshold; and
repeatedly performing the brightness comparing while the position of a pixel is changed.

2. The method of claim 1, wherein the item has a rectangular shape, and the image is photographed when all of four vertices of the item are exposed and the user's foot covers a part of edges of the item.

3. The method of claim 1, wherein the calculating of the positions of the vertices comprises:
calculating one or more feature points corresponding to a corner from the image;
calculating a convex polygon that surrounds a contour of the item from the image and then calculating candidate points of the vertices of the item through a simplification algorithm; and
comparing the one or more feature points with the candidate points to select the vertices.

4. The method of claim 1, wherein the calculating of the foot size or shape information from the image comprises calculating a difference between relative lengths of toes from the image to determine a shape type of the foot.

5. The method of claim 1, further comprising, before the acquiring of the image, providing a guide interface to photograph the image when a part of the user's foot comes in contact with the item.

6. The method of claim 1, wherein the calculating of the foot size or shape information from the image comprises:
calculating a region where the foot is located in the image; and
measuring an angle of hallux valgus of the foot from the calculated foot region.

7. The method of claim 1, wherein, when a shadow of the foot is photographed simultaneously in the image captured by photographing the foot, a boundary appears between a region of the shadow and the region of the foot.

8. The method of claim 7, further comprising distinguishing the region of the shadow and the region of the foot from each other using an edge detection algorithm.

9. The method of claim 1, further comprising performing histogram equalization in a portion excluding the first region from the image.

10. The method of claim 1, further comprising measuring a length of the foot using a length of a point where a vertical edge of the item and the region of the foot overlap.

11. The method of claim 1, further comprising measuring a width of the foot using a length of a point where a horizontal edge of the item and the region of the foot overlap.

12. The method of claim 1, further comprising, after the acquiring of the image and the calculating of the foot size or shape, providing a guide interface for shoe recommendation based on the size or shape information of the foot.

13. An application program combined with hardware and stored in a non-transitory computer-readable recording medium to execute the method of claim 1.

* * * * *